United States Patent
Won et al.

(10) Patent No.: US 9,279,014 B2
(45) Date of Patent: Mar. 8, 2016

(54) METHODS FOR PREPARING AN ACTIVE TNFR-FC FUSION PROTEIN

(75) Inventors: Hye Soon Won, Daejeon (KR); Byung Je Sung, Daejeon (KR); Yong Ho Ahn, Daejeon (KR); Sang Kyung Park, Daejeon (KR)

(73) Assignee: ARES TRADING S.A., Aubonne (CH)

(*) Notice: Subject to any disclaimer, the term of this patent is extended or adjusted under 35 U.S.C. 154(b) by 0 days.

(21) Appl. No.: 14/239,216

(22) PCT Filed: Aug. 17, 2012

(86) PCT No.: PCT/KR2012/006564
§ 371 (c)(1),
(2), (4) Date: Jul. 1, 2014

(87) PCT Pub. No.: WO2013/025079
PCT Pub. Date: Feb. 21, 2013

(65) Prior Publication Data
US 2014/0316114 A1    Oct. 23, 2014

(30) Foreign Application Priority Data
Aug. 17, 2011 (KR) .................. 10-2011-0081854

(51) Int. Cl.
*C07K 14/705* (2006.01)
*C07K 14/715* (2006.01)

(52) U.S. Cl.
CPC ....... *C07K 14/70578* (2013.01); *C07K 14/7151* (2013.01); *C07K 2319/30* (2013.01)

(58) Field of Classification Search
CPC ................. C07K 14/70578; C07K 14/7051; C07K 2319/30
See application file for complete search history.

(56) References Cited

U.S. PATENT DOCUMENTS

| 7,427,659 B2 * | 9/2008 | Shukla et al. | 530/350 |
| 8,283,138 B2 * | 10/2012 | Browning | C07K 14/70578 435/252.3 |
| 2014/0128577 A1 * | 5/2014 | Kulkarni | C07K 14/7151 530/387.3 |

FOREIGN PATENT DOCUMENTS

| CN | 102675465 A | * | 9/2012 |
| WO | 03/072060 A2 | | 9/2003 |
| WO | 2005/042569 A1 | | 5/2005 |
| WO | 2005/075498 A1 | | 8/2005 |
| WO | 2009/111347 A1 | | 9/2009 |

OTHER PUBLICATIONS

Kyogoku K et al., Journal of Bioscience and Engineering. 105(5):454-459, 2008.*
Evans D.R.H. et al., Journal of Chromatography. 1177:265-271, 2008.*
Zolodz M.D. et al. Journal of Chromatography. 1217:225-234, 2010.*
Machine translation of CN102675465A (Zhisheng, C.). "A purification method for recombined human II-type tumor necrosis factor receptor and antibody fusion protein".*
Kyogoku et al. 'Production of Recombinant Tumor Necrosis Factor receptor/Fc Fusion Protein by Genetically Manipulated Chickens'. Journal of Bioscience and Bioengineering. 2008, vol. 105, No. 5, pp. 454-459.
International Search Report for PCT/KR2012/006564. Dated Nov. 13, 2012. 5 pages.
Coffman et al. (2008) "High-throughput screening of chromatographic separations: I. Method development and column modeling," Biotechnol. Bioeng. 100(4):605-618.
Liu et al. (Jan. 2011) "Development of Production Procedure and Quality Control Method for Recombinant CHO Cells with Human Type II Tumor Necrosis Factor Receptor-Fc Fusion Gene," Chin. J. Biologicals. 24(1):70-74.—English abstract and drawings only.
McCue (2009) "Chapter 25: Theory and Use of Hydrophobic Interaction Chromatography in Protein Purification Applications," Methods Enzymol. 463:405-414.
Queiroz et al. (2001) "Hydrophobic interaction chromatography of proteins," J. Biotechnol. 87(2):143-159.
Tiwari et al. (2010) "Identification and characterization of native proteins of *Escherichia coli* BL-21 that display affinity towards Immobilized Metal Affinity Chromatography and Hydrophobic Interaction Chromatography Matrices," Protein Expr. Purif. 70(2):191-195.
Supplementary European Search Report corresponding to European Patent Application No. 12823797.1, dated Apr. 22, 2015, 7 pages.

* cited by examiner

*Primary Examiner* — Robert Landsman
(74) *Attorney, Agent, or Firm* — Lathrop & Gage LLP; Brian C. Trinique

(57) ABSTRACT

The present invention relates to a method for separating and preparing a TNFR-Fc fusion protein using hydrophobic interaction chromatography (HIC). More particularly, the present invention relates to a method for separating and preparing a highly pure active protein from clipped proteins due to displacement effect by adjusting the conductivity of a protein sample using a high concentration of salt solution and by adjusting a loading amount thereof, and a TNFR-Fc fusion protein prepared by the method.

22 Claims, 6 Drawing Sheets

In vitro biological activity

METHODS FOR PREPARING AN ACTIVE TNFR-FC FUSION PROTEIN

RELATED APPLICATIONS

This application is a 35 U.S.C. §371 filing of International Application No. PCT/KR2012/006564, filed Aug. 17, 2012, which claims priority to Korean Patent Application No. 10-2011-0081854, filed on Aug. 17, 2011, each of which is incorporated herein by reference in its entirety.

TECHNICAL FIELD

The present invention relates to a method for preparing a TNFR-Fc fusion protein using hydrophobic interaction chromatography (HIC). More particularly, the present invention relates to a method for preparing a highly pure active protein from a sample comprising a mixture of TNFR-Fc fusion proteins and clipped forms thereof due to displacement effect by adjusting the conductivity of a protein sample with a high concentration of salt solution and by adjusting a loading amount thereof, and a TNFR-Fc fusion protein prepared by the method.

BACKGROUND ART

Overexpression of TNF alpha (tumor necrosis factor alpha) in the human body is known to cause autoimmune diseases. TNFR (tumor necrosis factor receptor) is a TNF alpha receptor, and binds to an overexpressed TNF alpha to function as a therapeutic agent for autoimmune diseases. In addition, TNFR is fused with the human immunoglobulin G (IgG) Fc region to be expressed as an Fc fusion protein, thereby being used as a therapeutic protein drug.

TNFR-Fc can be prepared by fusion of 235 amino acids of TNFR with 232 amino acids of the Fc region including a hinge region. When TNFR-Fc is produced as a dimer by recombinant DNA technology, it shows a biological activity.

TNFR comprises 235 amino acids possessing 4 domains and a transmembrane region. TNFR has 22 cysteines, and all of them form disulfide bonds to have a steric structure. However, when TNFR-Fc is produced from animal cells, cysteines bind with each other at random, and thus they do not form disulfide bonds identical to those of a native protein. TNFR may be also partially truncated, and fail to form a correct TNFR-Fc dimer.

TNFR-Fc with incorrect disulfide bonds cannot show the proper biological activity due to a drastic reduction in the binding ability to TNF alpha. When the entire or a part of TNFR is truncated, it may also not exhibit the biological activity.

Therefore, when the TNFR-Fc dimers are produced using a recombinant DNA technology and an animal cell culture technique, active proteins, inactive proteins with incorrect disulfide bonds, aggregates, and clipped forms are produced at the same time, and thus a technique for isolating active proteins from the protein mixture is needed.

Therapeutic biomolecules must be purified with greater than 99% purity prior to human use. This degree of purification can be achieved through use of three or four liquid chromatography processes such as ion exchange chromatography, reversed phase chromatography, size exclusion chromatography, affinity (dye, metal, antibody, protein A, etc.) chromatography, and hydrophobic interaction chromatography which are required during the isolation process. The type and sequence of chromatographic processes chosen are based on physicochemical characteristics of contaminants that coexist with the target biomolecule. Usually, size exclusion chromatography is employed in a final step, because it removes protein aggregates and also exchanges the purified proteins into the final formulation buffer.

However, size exclusion chromatography negatively affects productivity because of the limited sample volume that can be loaded. Column load volume of sample greater than about 5% of the overall column volume results in diffusion-related band spreading and dilution as the solute band moves through the column. The volume limitation can be circumvented through the use of an ultrafiltration concentration step prior to column loading. Ultrafiltration concentration also introduces productivity losses due to non-specific binding of the protein to the membrane and other materials in the system, volume losses to tubing and pumps, and complications associated with equipment preparation, operation, and cleaning. Therefore, the purification process can clearly be simpler and productivity losses can be avoided by applying a concentrated target protein to hydrophobic interaction chromatography to obtain displacement effect. However, the separation method of the target protein using hydrophobic interaction chromatography requires different separation conditions depending on the type of the target protein, the expression vector including a polynucleotide encoding the protein, etc. Frequently, the known separation methods of the target protein cannot be applied in the separation of other target proteins or in the separation of the target protein prepared under different conditions. In the market for protein drugs, therefore, it is very important to investigate suitable conditions for separating a desired target protein with high purity and concentration.

DISCLOSURE OF INVENTION

Technical Problem

Based on this background, the present inventors have made many efforts to separate an active form of TNFR-Fc fusion protein with high purity and concentration. As a result, they found that only the active TNFR-Fc fusion protein fraction can be recovered with high purity using hydrophobic interaction chromatography having an advantage of low probability of protein denaturation without the use of an organic solvent by adjusting a loading amount of a protein sample per unit medium volume and by adjusting conductivity thereof, unlike the conventional techniques, thereby completing the present invention.

Solution to Problem

An object of the present invention is to provide a method for preparing an active form of TNFR (tumor necrosis factor receptor)-Fc fusion protein using hydrophobic interaction chromatography (HIC).

Another object of the present invention is to provide an active form of TNFR (tumor necrosis factor receptor)-Fc fusion protein prepared by the above method.

Advantageous Effects of Invention

The present invention provides a method for preparing an active protein from a sample comprising a protein mixture using hydrophobic interaction chromatography (HIC) by adjusting the conductivity of the protein sample using a high concentration of salt solution and by adjusting the loading amount thereof. Therefore, the method can be applied for the isolation of a highly pure active protein from recombinant proteins that are produced from animal cells by recombinant DNA technology.

BEST MODE FOR CARRYING OUT THE INVENTION

Figure 1:
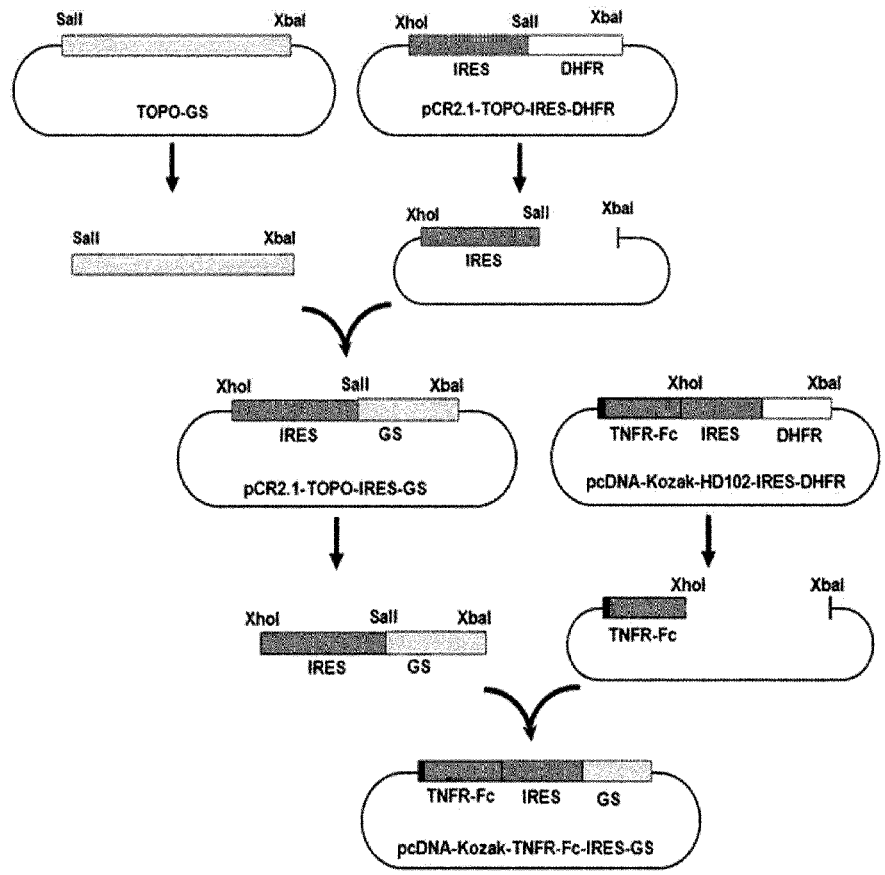
FIG. 1 is a schematic diagram showing the cloning method of pcDNA3.1-Kozak-TNFRII-Fc-IRES-GS of the present invention.

In one aspect to achieve the above objects, the present invention provides a method for preparing an active form of TNFR (tumor necrosis factor receptor)-Fc fusion protein using hydrophobic interaction chromatography (HIC).

Preferably, the method may comprises a) loading a sample comprising a mixture of TNFR-Fc fusion proteins produced in mammalian cells to the hydrophobic interaction chromatography (HIC) column pre-equilibrated with an equilibration buffer comprising one or more salts selected from the group consisting of sodium citrate, sodium sulfate, and sodium phosphate in an amount of 10 to 14 g/L bed per volume of chromatography resin; b) washing the column with a wash buffer comprising the same salt as in the equilibration buffer to remove clipped forms of TNFR-Fc fusion protein from the mixture of TNFR-Fc fusion proteins; and c) eluting the active form of TNFR-Fc fusion protein from the column with an elution buffer having a salt concentration lower than the equilibration buffer, but the method is not limited thereto.

When the TNFR-Fc fusion protein is produced by a host cell transformed with an expression vector comprising a polynucleotide encoding the TNFR-Fc fusion protein, cysteines of TNFR protein bind with each other at random, and thus they do not form disulife bonds identical to those of a native TNFR protein, or TNFR protein is also partially truncated, and thus fails to form a correct TNFR-Fc dimer, in addition to the formation of a dimer form of TNFR-Fc fusion protein that binds to TNF-alpha and shows a biological activity. Therefore, when the TNFR-Fc fusion protein is produced in a host cell, there is a need to separate only the active TNFR-Fc fusion protein having a biological activity identical or corresponding to that of the wild-type TNFR protein from the mixture of the active TNFR-Fc fusion protein, inactive TNFR-Fc fusion protein, or TNFR-Fc fusion protein aggregates. The method of the present invention is a method capable of separating the active TNFR-Fc fusion protein with high purity from the mixture of TNFR-Fc fusion proteins using hydrophobic interaction chromatography, and thus it can be effectively used for isolation of the active TNFR-Fc fusion protein.

As used herein, the term "TNFR (tumor necrosis factor receptor) protein" means a receptor protein binding to TNF-α. The TNFR includes TNFRI(p55) protein or TNFRII(p75) protein, preferably may be a TNFRII protein, but not limited thereto. The TNFRII may be interchangeable with TNFRSF1B (Tumor necrosis factor receptor superfamily member 1B). The TNFRII protein may be a TNFRII protein having 4 domains and a transmembrane region, and comprising 235 amino acids, but not limited thereto. Information about the TNFRI protein and TNFRII protein may be obtained from the known databases such as US NIH GenBank, and for example, it may be a protein having Accession number NP_001056 or P20333, but is not limited thereto.

The TNFR protein has an biological activity of binding to TNF-α, of which overexpression in the human body is known to cause various diseases, and thus it can be used for the treatment of TNF-α-mediated diseases such as autoimmune diseases. To achieve this, the immunoglobulin Fc region is fused with TNF-α protein to prepare a fusion protein having increased half-life.

As used herein, the term "TNFR (tumor necrosis factor receptor)-Fc fusion protein" means a product resulting from linkage of the entire or a part of TNFR protein with immunoglobulin Fc region by enzymatic action, or resulting from expression of two polypeptides into a single polypeptide by gene manipulation. In the TNFR-Fc fusion protein, the TNFR protein and the immunoglobulin Fc region may be directly linked with each other, or linked via a peptide linker, but is not limited thereto.

The TNFR-Fc fusion protein may be prepared by fusion of the entire or a part of TNFR protein with the immunoglobulin Fc region, and for example, by fusion of the amino acids from 1 to 235 positions of TNFRII protein with 232 amino acids of the immunoglobulin Fc region including a hinge region, but is not limited thereto. In addition, the TNFR-Fc fusion protein may be codon-optimized for expression in the host cells. For example, the TNFR-Fc fusion protein may be a TNFR-Fc fusion protein codon-optimized for CHO cells, defined by the amino acid sequence of SEQ ID NO. 1, but is not limited thereto. The TNFR-Fc fusion protein includes a protein comprising the amino acid sequence of SEQ ID NO. 1, and all proteins having amino acid sequences having 70% or higher homology, preferably 80% or higher homology, more preferably 90% or higher homology, much more preferably 95% or higher homology, and most preferably 98% or higher homology with the sequence, as long as the proteins substantially have an activity of binding to TNF-α. It is apparent that any type of protein variants having a deletion, modification, substitution or addition of some sequence may be within the scope of the present invention, as long as the sequence having the homology is an amino acid sequence having a biological activity that is substantially identical or corresponding to the TNFR (tumor necrosis factor receptor)-Fc fusion protein. In addition, the polynucleotide encoding the TNFR (tumor necrosis factor receptor)-Fc fusion protein includes a nucleotide sequence of SEQ ID NO. 2, and all nucleotide sequences having 70% or higher homology, preferably 80% or higher homology, more preferably 90% or higher homology, much more preferably 95% or higher homology, and most preferably 98% or higher homology with the sequence, as long as the nucleotide sequences substantially encode proteins having an activity of binding to TNF-α. It is also apparent that any type of nucleotide sequences encoding protein variants having a deletion, modification, substitution or addition of some sequence may be within the scope of the present invention, as long as the sequence having the homology is a nucleotide sequence encoding an amino acid sequence having a biological activity that is substantially identical or corresponding to the TNFR-Fc fusion protein. In one embodiment of the present invention, codonoptimization specific for CHO cells was performed.

As used herein, the term "immunoglobulin (Ig) Fc region" refers to a part of immunoglobulin that contains the heavy-chain constant region 2 (CH2), the heavy-chain constant region 3 (CH3), and a hinge region, excluding the variable regions of the heavy and light chains, the heavy-chain constant region 1 (CH1) and the light-chain constant region 1 (CL1) of the immunoglobulin. The immunoglobulin Fc region of the present invention includes a native amino acid sequence, and a sequence derivative thereof. An amino acid sequence derivative is a sequence that is different from the native amino acid sequence due to a deletion, an insertion, a non-conservative or conservative substitution or combinations thereof of one or more amino acid residues. In addition, the immunoglobulin Fc region may be a Fc region that is derived from IgG, IgM, IgE, IgA or IgD, or that is made by combinations thereof or hybrids thereof. Preferably, it is derived from IgG, which is known to enhance the half-life of binding proteins. More preferably, it is derived from IgG1, but is not limited thereto.

On the other hand, the term "combination", as used herein, means that polypeptides encoding single-chain immunoglobulin Fc regions of the same origin are linked to a single-chain polypeptide of a different origin to form a dimer or multimer. That is, a dimer or multimer may be formed from two or more fragments selected from the group consisting of IgG Fc, IgA Fc, IgM Fc, IgD Fc, and IgE Fc fragments.

The term "hybrid", as used herein, means that sequences encoding two or more immunoglobulin Fc regions of different origin are present in a single-chain immunoglobulin Fc region. In the present invention, various types of hybrids are possible. That is, domain hybrids may be composed of one to four domains selected from the group consisting of CH1, CH2, CH3 and CH4 of IgG Fc, IgM Fc, IgA Fc, IgE Fc and IgD Fc, and may include the hinge region. On the other hand, IgG is also divided into IgG1, IgG2, IgG3 and IgG4 subclasses, and the present invention includes combinations and hybrids thereof.

The TNFR-Fc fusion protein may be obtained by introducing the expression vector comprising the polynucleotide encoding the fusion protein into mammalian cells, and then expressing it therein, and for example, by introducing a vector comprising a polynucleotide encoding mutated GS (glutamine synthetase) enzyme and the TNFR-Fc fusion protein into mammalian cells, but is not limited thereto.

The mutated GS enzyme is an enzyme having a sequence containing a substitution of Arginine (R) for Glycine (G) at position 299 in the amino acid sequence of wild-type GS enzyme, and the expression vector comprising the polynucleotide encoding the TNFR-Fc fusion protein of the present invention may include the mutated GS enzyme. An example thereof may be a pcDNA3.1-Kozak-TNFRII-Fc-IRES-GS vector, but is not limited thereto.

In the present invention, the pcDNA3.1-Kozak-TNFRII-Fc-IRES-GS vector was used as the representative expression vector comprising the polynucleotide encoding the TNFR-Fc fusion protein, and transformed into CHO cells to express the TNFR-Fc fusion protein. The mixture of various forms of TNFR-Fc fusion proteins such as the active TNFR-Fc fusion protein, the clipped forms of TNFR-Fc fusion protein, the inactive TNFR-Fc fusion protein, or/and the TNFR-Fc fusion protein aggregate are included in the TNFR-Fc fusion proteins obtained by the above method. Therefore, it is necessary to isolate only the active TNFR-Fc fusion protein having a biological activity of binding to TNF-alpha. When the preparation method of the present invention is used, the active fusion protein and the aggregate can be obtained as separate fractions, and therefore, only the active fusion protein can be obtained with high purity.

The method for preparing the active TNFR-Fc fusion protein of the present invention comprises a) loading a sample comprising a mixture of TNFR-Fc fusion proteins to the hydrophobic interaction chromatography (HIC) column pre-equilibrated with an equilibration buffer.

The step a) is a step of loading the sample to the HIC column pre-equilibrated with an equilibration buffer.

The pre-equlibration of the column is conducted by treating the column with a high concentration of salt solution in order to equilibrate the chromatography column resin.

An example of the high concentration of salt solution may be a buffer solution comprising one or more salts selected from the group consisting of sodium citrate, sodium sulfate, and sodium phosphate, but the type of salt solution is not particularly limited, as long as it is able to equilibrate the hydrophobic interaction chromatography column of the present invention. For example, sodium citrate or sodium sulfate may be used as the salt, but the salt is not limited thereto. If the equilibration buffer comprises sodium citrate as the salt, its concentration may be 0.45 to 0.55 M, and the equilibration buffer may further comprise 50 to 100 mM sodium phosphate, but is not limited thereto. In addition, if the equilibration buffer comprises sodium sulfate as the salt, its concentration may be 0.70 to 0.72 M, and the equilibration buffer may further comprise 50 to 100 mM sodium phosphate, but is not limited thereto. In addition, pH of the equilibration buffer may be preferably 6.5 to 7.0, but is not limited thereto. More preferably, the equilibration buffer may be a buffer comprising 0.48 to 0.52 M sodium citrate and 50 to 70 mM sodium phosphate at pH 6.7 to 6.9, or a buffer comprising 0.71 to 0.72 M sodium sulfate and 50 to 70 sodium phosphate at pH 6.7 to 6.9, and most preferably, may be a buffer comprising 0.5 M sodium citrate and 50 mM sodium phosphate at pH 6.8, or a buffer comprising 0.72 M sodium sulfate and 50 mM sodium phosphate at pH 6.8, but is not limited thereto.

In one embodiment of the present invention, the buffer comprising 0.5 M sodium citrate and 50 mM sodium phosphate at pH 6.8, and the buffer comprising 0.72 M sodium sulfate and 50 mM sodium phosphate at pH 6.8 were used as the equilibration buffer.

As used herein, the term "hydrophobic interaction chromatography (HIC)" is used in the purification process of biomolecules, and it is based on a reversible interaction between a protein surface and an adsorbent of hydrophobic interaction chromatography. It is very useful in the separation of contaminants having an isoelectric point or a molecular weight similar to that of isoform protein, compared to ion exchange chromatography or size exclusion chromatography.

The type of the ligand used in the column of the hydrophobic interaction chromatography is not particularly limited, as long as the ligand can be used for the separation of the active TNFR-Fc fusion protein of the present invention, and examples thereof may include a butyl group, an octyl group, a phenyl group, and an alkyl group. The ligand may be preferably the butyl or phenyl group, and more preferably, the butyl group, but is not limited thereto. In one embodiment of the present invention, Butyl Sepharose 4 Fast Flow containing butyl ligands, manufactured by GE Healthcare, was used. The Butyl Sepharose 4 Fast Flow used is based on 90 μm beads of highly crosslinked 4% agarose matrix with butyl ligands coupled via ether linkages, and has high chemical, physical and thermal stabilities. Due to high hydrophobicity of the medium, it can be used to separate hydrophilic proteins.

The method for preparing the active TNFR-Fc fusion protein of the present invention comprises the step of a) loading a sample comprising a mixture of TNFR-Fc fusion proteins to the pre-equilibrated column.

As used herein, the term "a sample comparing a mixture of TNFR-Fc fusion proteins" may be a cell culture supernatant comprising the TNFR-Fc fusion proteins, a cell extract, or the partially purified cell culture supernatant or cell extract, but is not limited thereto. When the TNFR-Fc fusion proteins are produced in the host cells, the mixture of active TNFR-Fc fusion proteins, clipped TNFR-Fc fusion proteins having partial deletions of the TNFR-Fc fusion proteins, inactive TNFR-Fc fusion proteins with incorrect disulfide bonds, or/and the TNFR-Fc fusion protein aggregates is(are) included in the cell culture supernatant or cell extract.

The TNFR-Fc fusion protein is preferably expressed in the mammalian cells introduced with the expression vector comprising the polynucleotide encoding the fusion protein, and the supernatant is recovered. Then, it may be partially purified by one or more methods selected from the group consisting of affinity chromatography, ion exchange chromatography, and desalting, before loading it to the hydrophobic interaction chromatography, but is not limited thereto.

As used herein, the term "partially purified" means that proteins other than the desired active TNFR-Fc fusion protein exist even after performing one or more fractionation procedures such as chromatography. In one embodiment of the present invention, partial purification of the culture supernatant was performed using Protein A chromatography.

The mixture of TNFR-Fc fusion proteins may be a mixed protein sample, of which conductivity is adjusted with the high concentration of salt solution, before loading it to the hydrophobic interaction chromatography column. The salt solution may be a solution comprising a salt selected from the group consisting of sodium citrate, sodium sulfate and ammonium sulfate, but is not limited thereto. The conductivity of the TNFR-Fc fusion protein sample treated with the high concentration of salt solution is preferably adjusted within the range from 50 to 75 mS/cm.

When the high concentration of salt solution is a solution comprising sodium citrate, the conductivity is preferably adjusted within the range from 50 to 55 mS/cm, and when the high concentration of salt solution is a solution comprising sodium sulfate, the conductivity is preferably adjusted within the range from 65 to 75 mS/cm, but are not limited thereto. The protein sample preferably has the sodium citrate concentration of 0.45 to 0.55 M, more preferably 0.48 to 0.52 and most preferably 0.5 M. The protein sample preferably has the sodium sulfate concentration of 0.70 to 0.72 M, more preferably 0.71 to 0.72, and most preferably 0.72 M. In addition, pH of the protein sample may be 6.5 to 7.0, but is not limited thereto.

In one embodiment of the present invention, the TNFRII-Fc fusion protein sample was adjusted to have the conductivity of 50 to 52 mS/cm using a salt solution containing sodium citrate, and at this time, the final concentration of sodium citrate was 0.5 M. In addition, the sample was adjusted to have the conductivity of 65 to 75 mS/cm using a salt solution containing sodium sulfate, and at this time, the final concentration of sodium sulfate was 0.72 M (Experimental Example 1). In the present invention, hydrophobic interaction chromatography was also performed using sodium chloride as a salt, in addition to sodium citrate and sodium sulfate. However, the active TNFRII-Fc fusion proteins did not bind to the column even at a high concentration of sodium chloride from 0.75 M to 1.5 M, and were recovered as a Flow-through fraction (FIGS. 3 to 5), indicating that the type and concentration of the salt used are also important factors in the method of the present invention.

In Step a), the mixture of TNFR-Fc fusion proteins may be loaded in an amount of 10 to 14 g/L bed per volume of chromatography resin in order to facilitate the protein separation by displacement effect.

As used herein, the term "displacement effect" means a phenomenon in which an analyte having a weaker binding ability is not retained in the column resin and is rapidly eluted, when an analyte having a stronger binding ability exists at a high concentration. In the present invention, the target analyte, active TNFR-Fc fusion protein can be easily separated from the inactive protein and protein aggregates only by adjusting the conductivity because there is a large difference in hydrophobicity between them. However, the active protein cannot be easily separated from the clipped proteins using the existing hydrophobic interaction chromatography, due to a small difference in hydrophobicity between them. The present invention is characterized in that the clipped protein fraction can be easily removed from the active protein by the displacement effect when the loading amount of the protein sample is adjusted within the range from 10 to 14 g/L bed per volume of chromatography resin. More preferably, the protein sample may be loaded in an amount of 12 to 14 g/L bed per volume of chromatography resin. In one embodiment of the present invention, the displacement effects were compared according to the loading amount of protein. When the protein sample was loaded in an amount of 9.5 g/L bed less than 10 g/L bed, the clipped TNFRII-Fc fusion protein fraction and the active TNFRII-Fc fusion protein fraction were not easily separated. In contrast, when the protein sample was loaded in an amount of 13 g/L bed, the clipped fraction and the active fraction were clearly separated (Experimental Example 5, FIGS. 9 and 10).

In addition, the method of the present invention comprises the step of b) washing the column with a wash buffer to separate and remove the clipped TNFR-Fc fusion protein fraction.

The wash buffer may have the same composition as in the equilibration buffer, but is not limited thereto. When the column is washed with the wash buffer, the clipped TNFR-Fc fusion proteins are eluted. At this time, the eluted peak is designated as Peak 1 in the present invention.

In one embodiment of the present invention, the column was washed with the equilibration buffer used in equilibration, so as to remove the clipped proteins. In this regard, the used equilibration buffer was a buffer comprising 0.5 M sodium citrate and 50 mM sodium phosphate at pH 6.8 or a buffer comprising 0.72 M sodium sulfate and 50 mM sodium phosphate at pH 6.8.

Further, the method of the present invention includes the step of c) eluting the active TNFR-Fc fusion protein from the column with an elution buffer having a salt concentration lower than the equilibration buffer.

In hydrophobic interaction chromatography, the more hydrophobic the molecule, the less salt needed to promote binding to the column. Thus, the active TNFR-Fc fusion proteins can be separated from the inactive TNFR-Fc fusion proteins or the TNFR-Fc fusion protein aggregates by adjusting the salt concentration, because there is a difference in hydrophobicity between them. In the above step, therefore, the active TNFR-Fc fusion protein is eluted from the column by reducing interaction between the active TNFR-Fc fusion protein and the hydrophobic ligand using the elution buffer having a lower salt concentration than the equilibration buffer. In the present invention, the peak having the active TNFR-Fc fusion protein is designated as Peak 2.

The elution buffer is a buffer having a lower salt concentration than the equilibration buffer and the wash buffer, and its conductivity may be 40 to 47 mS/cm. When an elution buffer comprising sodium citrate is used, the elution buffer may comprise sodium citrate at a concentration of 0.35 to 0.4 M, more preferably 0.38 to 0.4 M, and most preferably 0.4 M, but is not limited thereto. When an elution buffer comprising sodium sulfate is used, the elution buffer may comprise sodium sulfate at a concentration of 0.35 to 0.56 M, more preferably 0.38 to 0.4 M and most preferably 0.4 M, but is not limited thereto. In addition, the elution buffer further comprises 50 to 100 mM sodium phosphate, but is not limited thereto. In one embodiment of the present invention, an elution buffer comprising 0.4 M sodium citrate and 50 mM sodium phosphate at pH 6.8, and an elution buffer comprising 0.4 M sodium sulfate and 50 mM sodium phosphate at pH 6.8 were used. pH of the elution buffer may be within the range from 6.5 to 7.0, but is not limited thereto. After performing step c), the conductivity becomes 40 to 47 mS/cm.

The method for preparing the active TNFR-Fc fusion protein may further comprise the step of d) separating a fraction comprising the inactive TNFR-Fc fusion proteins or the TNFR-Fc fusion protein aggregates from the column.

The above step is a step of eluting the fraction comprising the inactive proteins and the protein aggregates with a buffer comprising a salt concentration lower than the elution buffer or a buffer having no sodium citrate or sodium sulfate. At this time, the eluted peak is designated as Peak 3 in the present invention. The buffer to be used may have pH of 6.5 to 7.0, and 0 to 0.1 M sodium citrate or 0 to 0.1 M sodium sulfate, but is not limited thereto. In addition, the buffer may have pH ranging from 6.5 to 7.0, but is not limited thereto. Also, the buffer may have a conductivity of 4 to 6 mS/cm, comprise 50 to 70 mM sodium phosphate, or/and have pH of 6.7 to 6.9, but not limited thereto. In one embodiment of the present invention, a buffer comprising 50 mM sodium phosphate and pH 6.8 was used, and the conductivity was adjusted to 4 to 6 mS/cm.

As described above, the present invention provides a method for separating the active proteins from the mixture of the clipped proteins, the protein aggregates, the inactive proteins, and the active proteins using hydrophobic interaction chromatography. This method is characterized in that the clipped proteins having a weaker binding ability can be removed from the active proteins due to displacement effect by adjusting the conductivity of the sample loaded on the column using a high concentration of salt solution and by increasing the loading amount thereof. This method is also characterized in that the desired active TNFR-Fc fusion proteins can be separated and prepared at a high concentration by adjusting the concentration of a particular salt of hydrophobic interaction chromatography.

Figure 3:
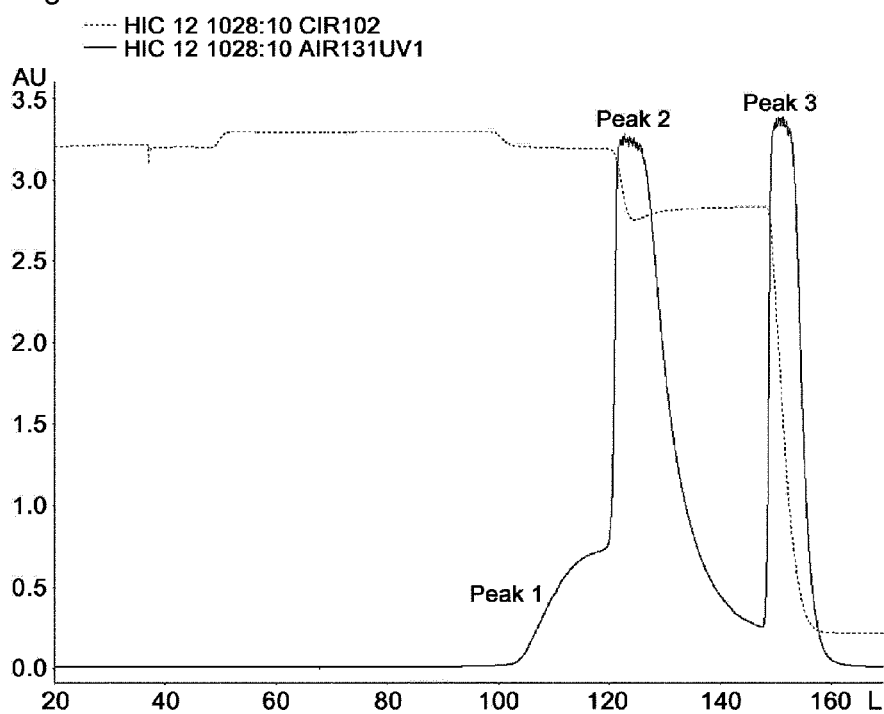
FIG. 3 shows a hydrophobic interaction chromatogram (HIC) using the sodium citrate according to one embodiment of the present invention.
Figure 6:
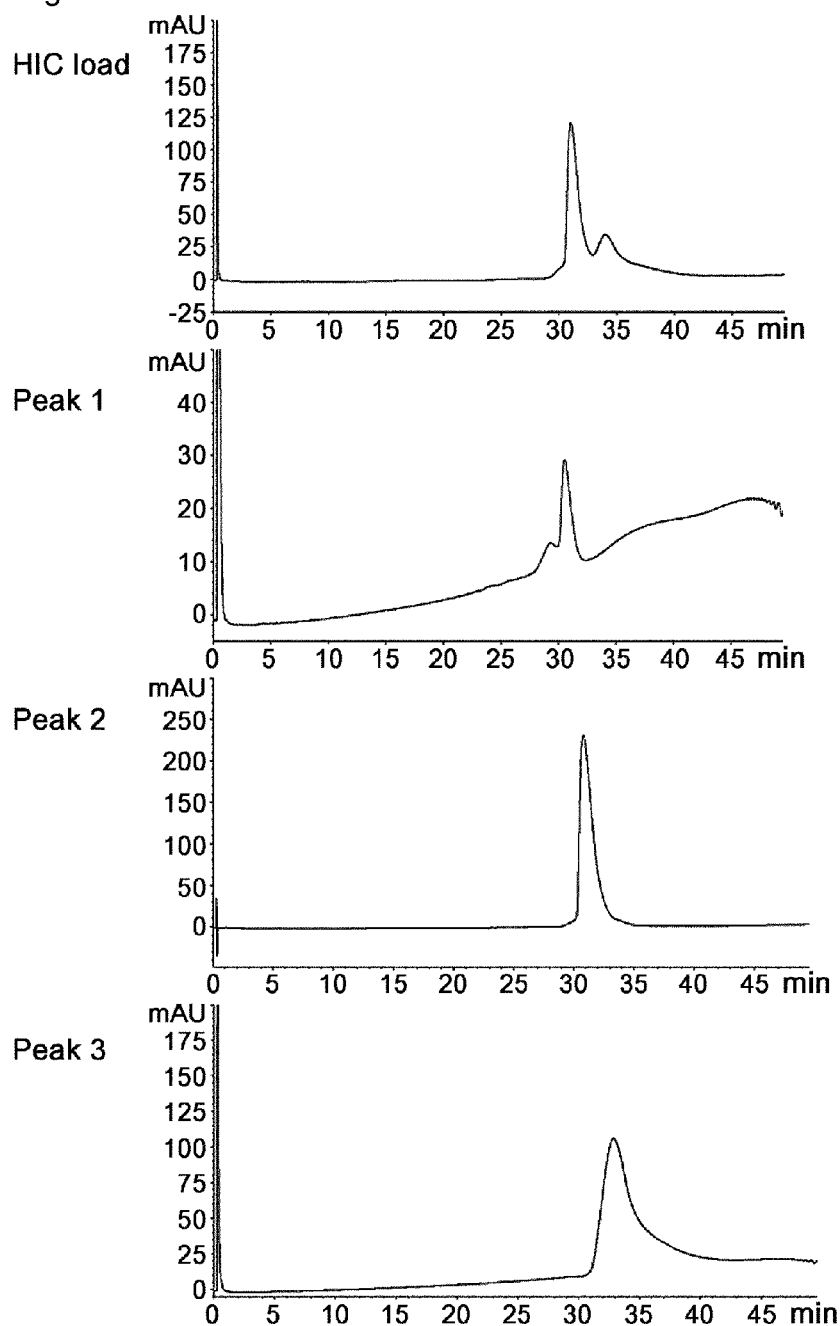
FIG. 6 shows hydrophobic HPLC analysis of each fraction according to one embodiment of the present invention.
Figure 7:
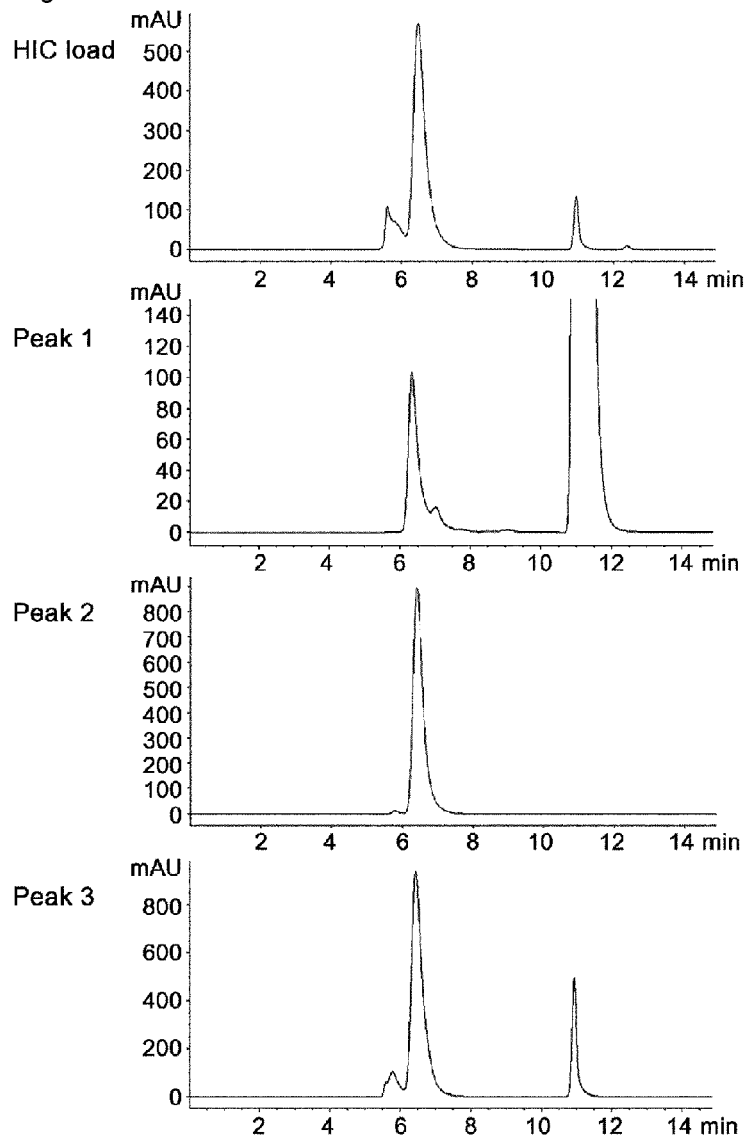
FIG. 7 shows size exclusion (SE)-HPLC analysis of each fraction according to one embodiment of the present invention.
Figure 8:
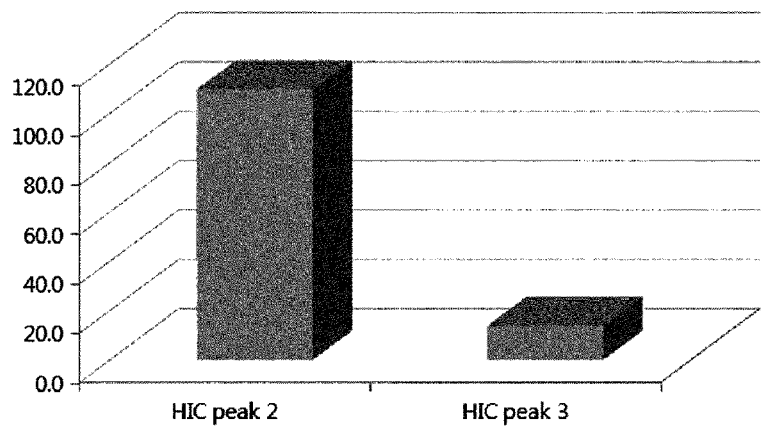
FIG. 8 shows in vitro biological activity of each fraction according to one embodiment of the present invention.

According to one embodiment of the present invention, the expression vector comprising the polynucleotides encoding GS having amino acid substitution at position 299 and the TNFRII-Fc fusion protein was transformed into animal cells, CHO (Examples 1 to 4), and the TNFRII-Fc fusion proteins were obtained therefrom. Then, hydrophobic interaction chromatography was performed in order to separate the active TNFRII-Fc fusion protein (Experimental Example 1). When the TNFRII-Fc fusion proteins are separated by the method of the present invention, the clipped TNFRII-Fc fusion protein, the active TNFRII-Fc fusion protein, and the TNFRII-Fc fusion protein aggregates were separated as Peaks 1, 2, and 3, respectively (FIGS. 3, 6 and 7). In addition, when the protein sample was loaded on the hydrophobic interaction chromatography column in an amount of 12 g/L bed or more, the peak corresponding to the clipped proteins, not separated when loaded in an amount of 9.5 g/L bed or less, was separated from the active protein peak (FIGS. 9 and 10), and the analyte corresponding to the obtained active protein peak was found to have the activity similar to that of pure active form (FIG. 8). According to the conventional techniques of purifying the TNFRII-Fc dimers, two fractions, that is, a fraction including the active proteins and a fraction including all of the inactive proteins, the protein aggregates, and the clipped proteins were separated. However, there have been no reports of separating three fractions, that is, a fraction including a large amount of the clipped proteins, a fraction including the active proteins, and a fraction including the inactive proteins and the protein aggregates. In the present invention, these three fractions were separated, and the activity of the fraction comprising the active TNFRII-Fc fusion protein was found to be similar to that of pure active form, indicating that the method of the present invention is able to prepare the active TNFRII-Fc fusion protein with high purity, compared to the conventional techniques.

Therefore, the method of the present invention can be used to purify the highly pure active TNFRII-Fc fusion proteins (for example, etanercept) having a biological activity by removing the clipped TNFRII-Fc fusion proteins, which are hardly separated by conventional methods.

In another aspect, the present invention provides an active TNFR-Fc fusion protein that is prepared by the above method.

Descriptions of the method and TNFR-Fc fusion protein are the same as above.

Mode for the Invention

Hereinafter, the present invention will be described in more detail with reference to Examples. However, these Examples are for illustrative purposes only, and the invention is not intended to be limited by these Examples.

Example 1

Synthesis of TNFRII-Fc Fusion Protein-Encoding Gene

In order to examine the expression level of a recombinant protein produced using a recombinant protein expression vector system, a TNFRII-Fc fusion protein was used as a desired protein.

The fusion protein-encoding gene (SEQ ID NO. 2) was synthesized by GeneArt Inc., so as to meet the following criteria: (1) it must include a TNFR signal sequence (2) it must express the TNFR amino acids at position from 1 to 235 (3) it must be codon-optimized for CHO cells in order to be transfected into CHO cells (4) it must have a NheI restriction site at 5'-end and a NotI restriction site at 3'-end, considering insertion into a pcDNA3.1 vector of Invitrogen.

Base sequence of the synthesized fusion protein-encoding gene was finally analyzed using a VectorNTI program.

Example 2

Construction of Expression Vector Including TNFRII-Fc Fusion Protein-Encoding Gene In order to acquire a DHFR system that is a common recombinant protein expression system, a hamster DHFR (dihydrofolate reductase) gene was cloned.

Specifically, in order to obtain the hamster DHFR gene, a pSVA3 vector (ATCC 77273) having a mutant type of hamster DHFR gene was purchased, and then a wild type of DHFR gene was obtained by performing point mutation using the DHFR gene as a template. In addition, an IRES sequence was obtained by PCR from a Clontech vector (Cat. #6029-1, PT3267-5) having the corresponding DNA sequence.

The obtained DHFR gene and IRES (Internal ribosome entry site) sequence were cloned into a pCR2.1 vector so as to construct a pCR2.1-IRES-DHFR expression vector.

Each of the TNFR-Fc-inserted pcDNA3.1-TNFR-Fc vector obtained in Example 1 and the obtained pCR2.1-IRES-DHFR vector was digested with restriction enzymes, SalI and XbaI, and ligated so as to obtain a TNFR-Fc-inserted pcDNA3.1-TNFR-Fc-IRES-DHFR expression vector. In order to clone it into a vector having a kanamycin-resistant gene, the kanamycin-resistant gene was obtained from a pAC-GFP vector (#632483) of Clontech, so as to introduce a Kan/Neo gene. The vector is a vector having a Kozak sequence at a transcription initiation sequence of the TNFR-Fc gene and the Kan/Neo gene as an antibiotic selection marker, and it was used as a basic frame for cloning 4 different expression vector systems in order to compare the expression levels of the recombinant protein using CHO cells.

Example 3

Cloning of Hamster GS Gene and Preparation of Mammalian Protein-Expressing Vector pcDNA3.1-Kozak-TNFRII-Fc-IRES-GS In order to acquire the GS DNA, a hamster cell line, CHO DG44 (Invitrogen, 12609-012) was cultured, and then a total RNA was isolated using a TRIZOL reagent (Invitrogen). RT-PCR was performed using the obtained total RNA so as to obtain cDNA. PCR (25 cycles of denaturation at 94° C. for 5 minutes; denaturation at 94° C. for 30 seconds, annealing at 50° C. for 30 seconds, elongation at 72° C. for 90 seconds; and elongation at 72° C. for 7 minutes) was performing using the obtained cDNA as a template and a pair of primers (GS SalI-F primer, GS XbaI-R primer) for acquisition of the following GS gene, so as to obtain a PCR product.

```
GS SalI-F:
                                    (SEQ ID NO. 3)
5'-gtcgacatggccacctcagcaagttccc-3'

GS XbaI-R:
                                    (SEQ ID NO. 4)
5'-tctagattagtttttgtattggaaaggg-3'
```

The obtained PCR product was electrophoresed on a 0.8% agarose gel, and then the corresponding band was cut, followed by clean-up using a Quiagen Cleaning kit (#28204). Then, the resultant was inserted into a gene cloning vector, pGEMT vector (Promega, USA). The PCR product-inserted pGEMT vector was introduced into a TOP10 cell so as to obtain a total of 10 colonies. A base sequence (SEQ ID NO. 5) and an amino acid sequence (SEQ ID NO. 6) encoded by the base sequence were analyzed. As a result, it was found that one amino acid differs from the amino acid sequence encoded by the hamster GS gene (GenBank: X03495.1) known in the NCBI GenBank. The cloned GS gene codes for a GS enzyme having a sequence containing a substitution of Arginine (R) for Glycine (G) at position 299 in the amino acid sequence of wild-type GS enzyme.

A fragment obtained by treating the pGEMT-GS with SalI and XbaI restriction enzymes was inserted into a TOPO-IRES-DHFR vector that was previously digested with SalI and XbaI restriction enzymes, so as to obtain a pCR2.1-TOPO-IRES-GS gene.

Figure 2:
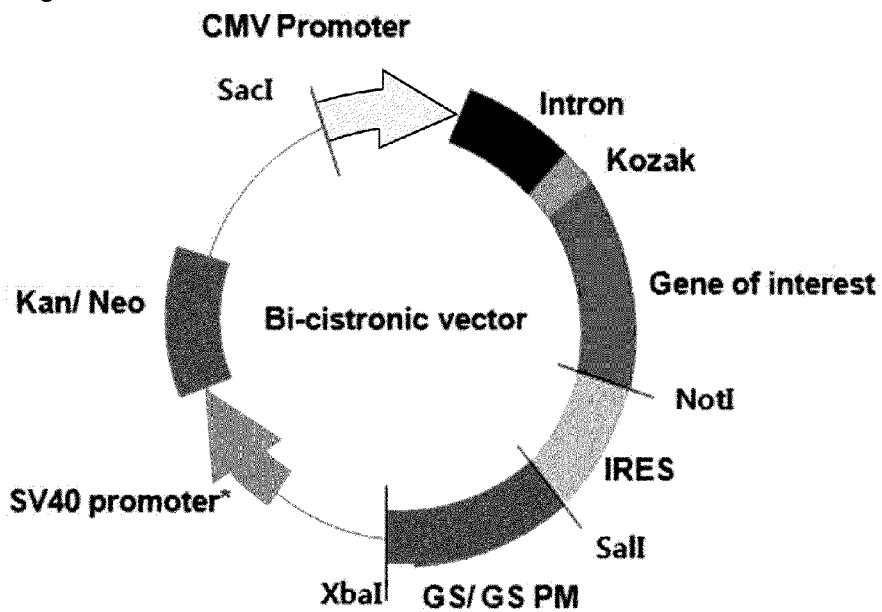
FIG. 2 is a cleavage map showing pcDNA3.1-kozak-TNFRII-Fc-IRES-GS, which is a recombinant expression vector including a TNFRII-Fc-encoding gene of the present invention.

Next, in order to connect the TNFR-Fc gene and the IREF-GS gene, the TNFRII-Fc-IRES-DHFR gene and the IRES-GS fragment digested with XhoI and XbaI were ligated so as to construct a kozak-TNFR-Fc-IRES-GS vector ("IRES-GS vector") (FIG. 1). FIG. 1 is a schematic diagram showing the cloning method of pcDNA3.1-Kozak-TNFRII-Fc-IRES-GS of the present invention. In addition, a schematic diagram of the vector is shown in FIG. 2.

Example 4

Preparation of Sample to be Applied to Hydrophobic Interaction Chromatography

CHO (Chinese hamster ovary) cells were introduced with pcDNA3.1-Kozak-TNFRII-Fc-IRES-GS vector comprising a TNFRII-Fc producing gene by lipofectamine 2000 (Invitrogen). The gene-introduced CHO cell line was cultured in a flask or bioreactor using a DMEM/F12 (Dulbecco's Modified Eagle Medium: Nutrient Mixture F-12) medium supplemented with 10% fetal bovine serum (FBS). The culture broth was filtered using a depth filter to remove cells, and microfiltration was performed again to remove cell debris. The supernatant was collected, and partially purified by Protein A chromatography. The pH of the purification fraction was adjusted to within the range from 3.6 to 3.8 using a 100 mM citric acid or phosphoric acid (pH 2.1).

A solution of 1 M sodium citrate and 75 mM sodium phosphate (pH 6.8) was mixed at a volume ratio of approximately 1:1. The solution was added under stirring until the conductivity reached 50 to 52 mS/cm at room temperature. After the addition, the mixture was filtered using a 0.2 μm filter.

Experimental Example 1

Hydrophobic Interaction Chromatography

Experimental Example 1-1

Hydrophobic Interaction Chromatography Using Sodium Citrate

A glass column was packed with Butyl Sepharose 4 Fast Flow (GE Healthcare) in a length of 8 cm or longer. A buffer solution (pH 6.8) of 0.5 M sodium citrate and 50 mM sodium phosphate (referred to as Buffer I) and a buffer solution (pH 6.8) of 50 mM sodium phosphate (referred to as Buffer J) were prepared.

3 column volumes of Buffer I as an equilibration buffer was applied to the packed column to equilibrate the column. After completion of the equilibration, the solution prepared in Example 4 was applied to the column in an amount of 12 grams per column liter or more. After completion of the injection, the column was washed with 2 column volumes of Buffer I as a wash buffer. At this time, the eluted fraction was designated as Peak 1.

Next, the elution buffer was made to have a composition of 80% Buffer I and 20% Buffer J, and then the conductivity was adjusted using the buffer. When signals of UV detector increased, a fraction was collected. At this time, the eluted fraction was designated as Peak 2. Peak 2 could be collected from 1.5 to 3.5 column volumes.

Next, the buffer was made to have a composition of 100% Buffer J, and then the column was washed with 3 column volumes of Buffer J. At this time, the eluted fraction was designated as Peak 3.

As a result of the hydrophobic interaction chromatography, the chromatogram of FIG. 3 was obtained. As shown in FIG. 3, Peak 1, Peak 2, and Peak 3 were separated. It can be seen that the clipped form was included in Peak 1, the active form was included in Peak 2, and the inactive form and protein aggregates were included in Peak 3.

Experimental Example 1-2

Hydrophobic Interaction Chromatography Using Sodium Sulfate

A column was packed with Butyl Sepharose 4 Fast Flow in a length of 10 cm or longer. A buffer solution (pH 6.8) of 0.72 M sodium sulfate and 50 mM sodium phosphate (hereinafter, referred to as 'Buffer S') and a buffer solution of 50 mM sodium phosphate (hereinafter, referred to as 'Buffer J') were prepared.

3 column volumes of Buffer S were applied to the packed column to equilibrate the column. After completion of the equilibration, the protein solution, in which the final concentration of sodium sulfate was adjusted to 0.72 M with a buffer (pH 6.8) of 1.2 M sodium sulfate and 50 mM sodium phosphate, was applied to the column in an amount of 11 grams per column liter or more. The protein solution had the conductivity ranging from 65 to 75 mS/cm. After completion of the injection, the column was washed with 2 column volumes of Buffer S. Next, the composition of Buffer S was reduced to 100-30% for 30 column volumes, and subsequently, reduced to 30-0% for 3 column volumes. The chromatogram resulting from the above hydrophobic interaction chromatography is shown in FIG. 4.

Figure 4:
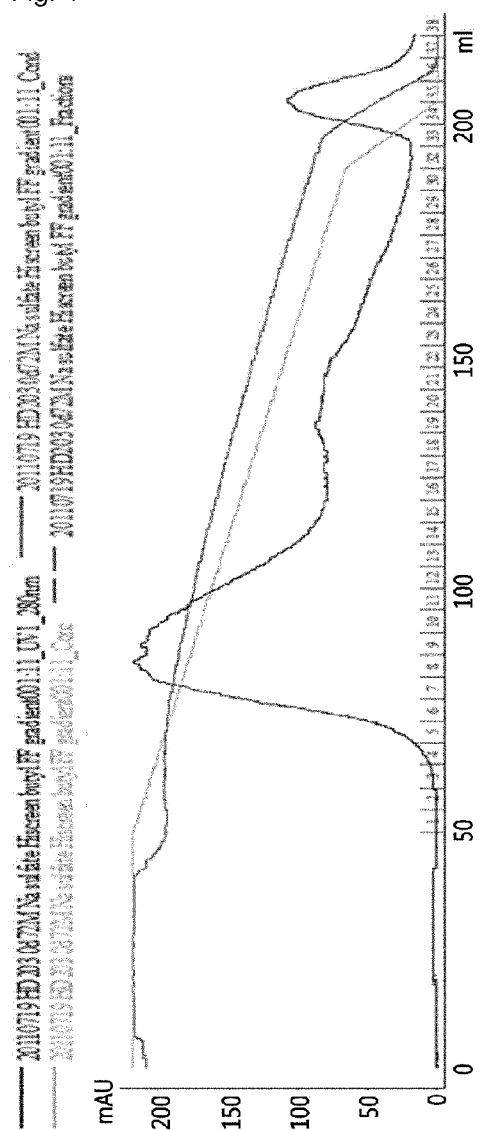
FIG. 4 shows a hydrophobic interaction chromatogram (HIC) using the sodium sulfate according to one embodiment of the present invention.

As shown in FIG. 4, the TNFRII-Fc fusion protein was found to be adsorbed onto the column at the sodium sulfate concentration of 0.72 M.

This result indicates that the active TNFRII-Fc fusion protein can be separated using sodium sulfate as the salt of the present invention, in addition to sodium citrate.

Experimental Example 1-3

Hydrophobic Interaction Chromatography Using Sodium Chloride

A column was packed with Butyl Sepharose 4 Fast Flow in a length of 10 cm or longer. A buffer solution (pH 7.2) of 0.75 M sodium chloride and 50 mM Tris-HCl (hereinafter, referred to as 'Buffer X'), a buffer solution (pH 7.2) of 1.0 M sodium chloride and 50 mM Tris-HCl (hereinafter, referred to as 'Buffer Y'), a buffer solution (pH 7.2) of 1.5 M sodium chloride and 50 mM Tris-HCl (hereinafter, referred to as 'Buffer Z'), and a buffer solution (pH 7.2) of 50 mM Tris-HCl (hereinafter, referred to as 'Buffer T') were prepared.

3 column volumes of Buffer X were applied to the packed column to equilibrate the column. After completion of the equilibration, the protein solution, in which the final concentration of sodium chloride was adjusted to 0.75 M with a buffer (pH 7.2) of 1.5 M sodium chloride and 50 mM Tris-HCl, was applied to the column in an amount of 4 grams per column liter or more. After completion of the injection, the column was washed with 2 column volumes of Buffer X. Next, the composition of Buffer X was reduced to 100-0% for 20 column volumes. In addition, the same procedures were also performed for Buffer Y and Buffer Z. The chromatogram resulting from the above hydrophobic interaction chromatography is shown in FIG. 5.

Figure 5:
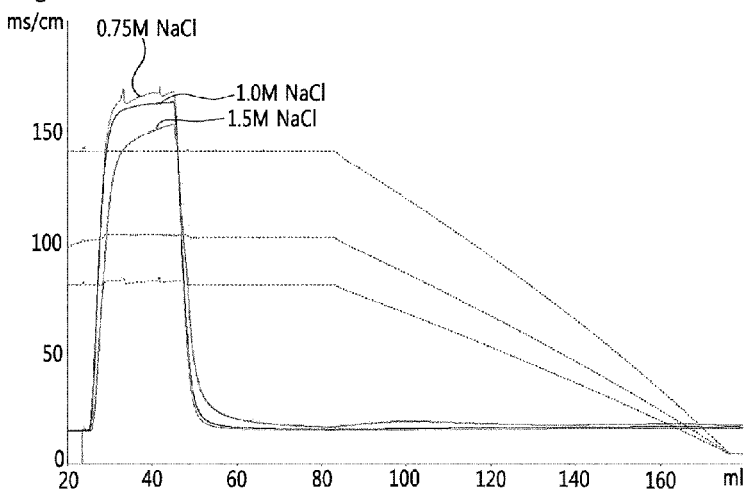
FIG. 5 shows a hydrophobic interaction chromatogram (HIC) using the sodium chloride according to one embodiment of the present invention.

As shown in FIG. 5, it was found that the TNFRII-Fc fusion protein was not adsorbed onto the column at the high concentration of sodium chloride, and recovered as a flow-through fraction.

These results indicate that the active TNFRII-Fc fusion protein of the present invention cannot be separated only by adjusting the conductivity, and the type and concentration of a particular salt is important in the separation.

Experimental Example 2

Hydrophobic-HPLC

The samples obtained from each step of Example 1-1 were subjected to hydrophobic-HPLC. In hydrophobic-HPLC, a Butyl NPR column (Tosoh Bioscience) was used, and mobile phase A was a solution (pH 7.0) of 1.8 M ammonium sulfate and 100 mM sodium phosphate, and mobile phase B was a solution (pH 7.0) of 100 mM sodium phosphate. For the initial 5 minutes, the mobile phase A composition was maintained at 100% and at a flow rate of 1 ml/min, followed by a linear gradient of the mobile phase A from 100% to 0% for 45 minutes. The results are shown in FIG. 6.

As shown in FIG. 6, in Peak 1, a fraction of Peak 1 is dominant but coexists with Peak 2. Peak 2 was found to include a single fraction of the active form. In Peak 3, a fraction of Peak 3 is only dominant without the fraction of the active form.

This result indicates that the preparation method of the TNFRII-Fc fusion protein of the present invention is effectively used to separate only the active form thereof.

Experimental Example 3

Size-Exclusion (SE)-HPLC

The samples obtained from each step of Experimental Example 1-1 were subjected to SE-HPLC. SE-HPLC is a method of separating proteins according to their size, and the clipped proteins and the protein aggregates can be separated according to retention time. A TSK-GEL3000SWXL column (Tosoh Bioscience; 7.8 mm ID*30 cm H) was equilibrated with PBS at a flow rate of 1 ml/min, and 20 μg of the protein was loaded for analysis. The results are shown in FIG. 7.

As shown in FIG. 7, a smaller peak was observed next to a main peak in Peak 1, and this peak represents the clipped forms with a smaller size. Peak 2 was detected as a single peak in SE-HPLC. In Peak 3, two peaks were eluted prior to the main peak, and these peaks represent protein aggregates.

This result indicates that the preparation method of the TNFRII-Fc fusion protein of the present invention is effectively used to separate only the active TNFRII-Fc fusion protein from the mixture of the TNFRII-Fc fusion proteins.

Experimental Example 4

In Vitro Biological Activity

The binding of TNF alpha with the fractions of Peak 2 and Peak 3 of Example 1-1 was examined. Peak 2 fraction or Peak 3 fraction was properly diluted, and then bound to a solid surface coated with anti IgFc antibody. After treatment with TNF alpha, binding of the fractions of Peak 2 and Peak 3 with TNF alpha was examined by HRP color development. The results are shown in FIG. 8.

As shown in FIG. 8, when a binding unit was regarded as 100, Peak 2 exhibited a value corresponding to 100, but Peak 3 exhibited a value of 20 or less, indicating that the method of the present invention is performed to effectively separate the active form and the inactive form from each other.

Experimental Example 5

Comparison of Displacement Effect According to Protein Amount Loaded in Hydrophobic Interaction Chromatography The analysis was performed in the same manner as in Experimental Example 1-1 using the same samples, except varying the sample loading amount per column unit volume. In Experimental Example 1-1, 12 g/L bed of the solution prepared in Example 4 was loaded to the column, whereas 9.5 g/L bed and 13 g/L bed thereof were loaded to the column in the present Experimental Example. The results are shown in FIGS. 9 and 10.

Figure 9:
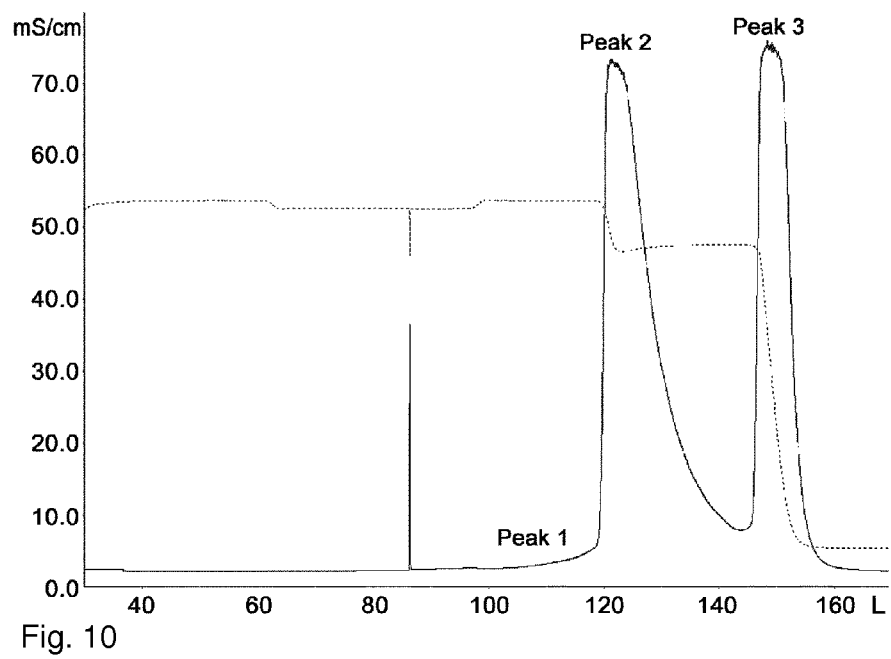
FIG. 9 shows a hydrophobic interaction chromatogram (HIC) when the protein is loaded in an amount of 9.5 g/L bed according to one embodiment of the present invention.
Figure 10:
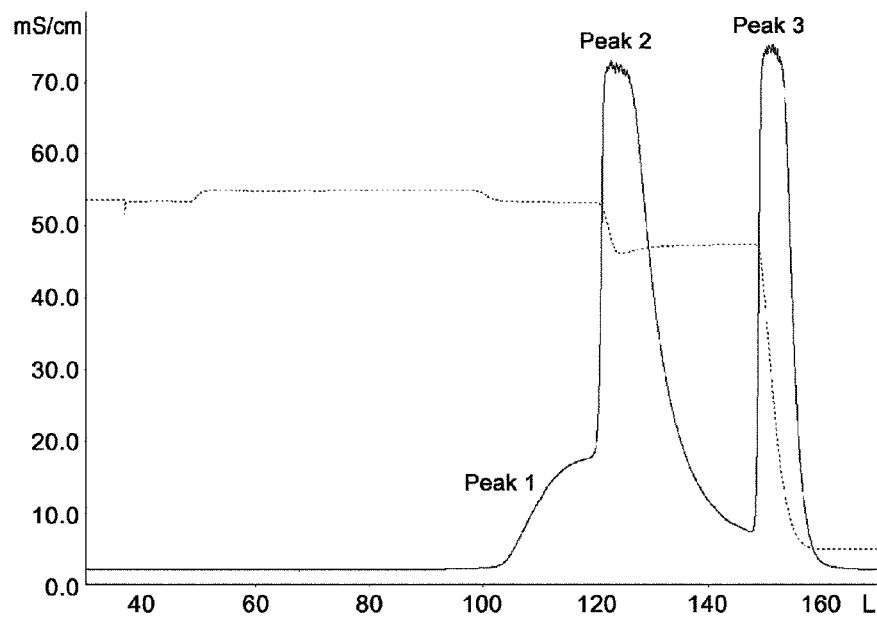
FIG. 10 shows a hydrophobic interaction chromatogram (HIC) when the protein is loaded in an amount of 13 g/L bed according to one embodiment of the present invention.

As shown in FIG. 9, when the smaller amount (9.5 g/L bed) was loaded, Peak 1 of the clipped protein fraction was not separated from Peak 2. On the contrary, as shown in FIG. 10, when the larger amount (13 g/L bed) was loaded, Peak 1 of the clipped protein fraction was clearly separated from Peak 2 of the active protein fraction.

This result indicates that the amount of the protein loaded for purification of the TNFRII-Fc fusion protein of the present invention is an important factor in the effective separation of the active protein.

The invention claimed is:

1. A method for preparing an active TNFR (tumor necrosis factor receptor)-Fc fusion protein, comprising:
    a) loading a sample comprising a mixture of TNFR-Fc fusion proteins produced in mammalian cells to a hydrophobic interaction chromatography (HIC) column pre-equilibrated with an equilibration buffer comprising one or more salts selected from the group consisting of sodium citrate, sodium sulfate, and sodium phosphate, wherein the mixture of TNFR-Fc fusion protein is loaded in an amount of 10 to 14 g/L bed volume of chromatography resin;
    b) washing the column with a wash buffer comprising the same salt as in the equilibration buffer to remove clipped forms of TNFR-Fc fusion protein from the mixture of TNFR-Fc fusion proteins; and
    c) eluting the active TNFR-Fc fusion proteins from the column with an elution buffer having salt concentration lower than the equilibration buffer.

2. The method according to claim 1, wherein the equilibration buffer of step a) is a buffer comprising 0.45 to 0.55 M sodium citrate and 50 to 100 mM sodium phosphate.

3. The method according to claim 1, wherein the equilibration buffer of step a) is a buffer comprising 0.70 to 0.72 M sodium sulfate and 50 to 100 mM sodium phosphate.

4. The method according to claim 1, wherein the equilibration buffer has pH ranging from 6.5 to 7.0.

5. The method according to claim 2, wherein the equilibration buffer comprises 0.48 to 0.52 M sodium citrate and 50 to 70 mM sodium phosphate at pH 6.7 to 6.9.

6. The method according to claim 3, wherein the equilibration buffer comprises 0.71 to 0.72 M sodium sulfate and 50 to 70 mM sodium phosphate at pH 6.7 to 6.9.

7. The method according to claim 1, wherein a ligand of the column is selected from the group consisting of a butyl group, an octyl group, a phenyl group, and an alkyl group.

8. The method according to claim 1, wherein the TNFR-Fc fusion protein of step a) is produced in mammalian cells introduced with a pcDNA3.1-Kozak-TNFRII-Fc-IRES-GS vector.

9. The method according to claim 1, wherein the TNFR-Fc fusion protein is partially purified by one or more methods selected from the group consisting of affinity chromatography, ion exchange chromatography, and desalting, before loading it to the column.

10. The method according to claim 1, wherein the sample comprising the mixture of TNFR-Fc fusion proteins is adjusted to have the conductivity of 50 to 75 mS/cm, before loading.

11. The method according to claim 10, wherein the conductivity is adjusted with one or more salts selected from the group consisting of sodium citrate, sodium sulfate and ammonium sulfate.

12. The method according to claim 1, wherein the sample comprising the mixture of TNFR-Fc fusion proteins is adjusted with sodium citrate to have the conductivity of 50 to 55 mS/cm, before loading.

13. The method according to claim 1, wherein the sample comprising the mixture of TNFR-Fc fusion proteins is adjusted with sodium sulfate to have the conductivity of 65 to 75 mS/cm, before loading.

14. The method according to claim 1, wherein the wash buffer of step b) has the same composition as in the equilibration buffer of step a).

15. The method according to claim 1, wherein step c) is to elute the active TNFR-Fc fusion protein with an elution buffer having a conductivity of 40 to 47 mS/cm.

16. The method according to claim 1, wherein the elution buffer of step c) comprises sodium citrate ranging from 0.35 to 0.4 M.

17. The method according to claim 1, wherein the elution buffer of step c) comprises sodium sulfate ranging from 0.35 to 0.56 M.

18. The method according to claim 15, wherein the elution buffer has pH ranging from 6.5 to 7.0.

19. The method according to claim 16, wherein the elution buffer comprises 0.38 to 0.4 M sodium citrate and 50 to 70 mM sodium phosphate at pH 6.7 to 6.9.

20. The method according to claim 17, wherein the elution buffer comprises 0.38 to 0.4 M sodium sulfate and 50 to 70 mM sodium phosphate at pH 6.7 to 6.9.

21. The method according to claim 1, further comprising d) separating a fraction comprising inactive TNFR-Fc fusion proteins or TNFR-Fc fusion protein aggregates from the column with a buffer having pH 6.5 to 7.0 and conductivity of 4 to 6 mS/cm.

22. The method according to claim 21, wherein the buffer used in step d) comprises 50 to 70 mM phosphate at pH 6.7 to 6.9.

\* \* \* \* \*

SEQUENCE LISTING

```
<160> NUMBER OF SEQ ID NOS: 6

<210> SEQ ID NO 1
<211> LENGTH: 467
<212> TYPE: PRT
<213> ORGANISM: Artificial Sequence
<220> FEATURE:
<223> OTHER INFORMATION: Description of Artificial Sequence: Synthetic
      TNFRII-Fc polypeptide

<400> SEQUENCE: 1

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
            85                  90                  95

Thr Cys Arg Pro Gly Trp Tyr Cys Ala Leu Ser Lys Gln Glu Gly Cys
        100                 105                 110

Arg Leu Cys Ala Pro Leu Arg Lys Cys Arg Pro Gly Phe Gly Val Ala
    115                 120                 125

Arg Pro Gly Thr Glu Thr Ser Asp Val Val Cys Lys Pro Cys Ala Pro
130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
            165                 170                 175

Val Cys Thr Ser Thr Ser Pro Thr Arg Ser Met Ala Pro Gly Ala Val
        180                 185                 190
```

```
His Leu Pro Gln Pro Val Ser Thr Arg Ser Gln His Thr Gln Pro Thr
            195                 200                 205

Pro Glu Pro Ser Thr Ala Pro Ser Thr Ser Phe Leu Leu Pro Met Gly
    210                 215                 220

Pro Ser Pro Pro Ala Glu Gly Ser Thr Gly Asp Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
                260                 265                 270

Ile Ser Arg Thr Pro Glu Val Thr Cys Val Val Val Asp Val Ser His
            275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
                340                 345                 350

Glu Lys Thr Ile Ser Lys Ala Lys Gly Gln Pro Arg Glu Pro Gln Val
            355                 360                 365

Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
                420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
450                 455                 460

Pro Gly Lys
465

<210> SEQ ID NO 2
<211> LENGTH: 1401
<212> TYPE: DNA
<213> ORGANISM: Artificial Sequence
<220> FEATURE:
<223> OTHER INFORMATION: Description of Artificial Sequence: Synthetic
      TNFRII-Fc polynucleotide

<400> SEQUENCE: 2
ctgcctgccc aggtggcctt caccccttac gcccctgagc tggctccac  ctgccggctg    60 cgggagtact acgaccagac cgcccagatg tgctgctcca agtgctcccc tggccagcac   120
gccaaggtgt ctgcaccaa gacctccgac accgtgtgcg acagctgcga ggactccacc   180
tacacccagc tgtggaactg ggtgcccgag tgcctgtcct gcggctcccg gtgctcctcc   240
gaccaggtgg agacccaggc ctgcacccgg gagcagaacc ggatctgcac ctgcaggcct   300
ggctggtact  cgccctgtc caagcaggag ggctgccgcc tgtgcgcccc tctgcggaag   360
tgccggcctg gcttcggcgt ggccaggcct ggcaccgaga ccagcgacgt ggtgtgcaag   420
```

```
ccttgcgccc ctggcaccttt ctccaacacc acctcctcca ccgacatctg ccggcctcac    480
cagatctgca acgtggtggc catccctggc aacgcctcca tggacgccgt gtgcacctcc    540
acctccccca cccggtctat ggcccctggc gctgtgcacc tgcctcagcc tgtgtccacc    600
cggtcccagc acaccagcc tacccctgag ccctccaccg ccccttctac cagcttcctg    660
ctgcctatgg gccctagccc tcctgccgag ggctccaccg gcgacgagcc taagtcctgc    720
gacaagaccc acacctgccc tccctgccct gccctgagc tgctgggcgg accttccgtg    780
ttcctgttcc ctcctaagcc taaggacacc ctgatgatct cccggacccc tgaggtgacc    840
tgcgtggtgg tggacgtgtc ccacgaggat cctgaggtga agttcaattg gtacgtggac    900
ggcgtggagg tgcacaacgc caagaccaag cctcgggagg agcagtacaa cagcacctac    960
cgggtggtgt ccgtgctgac cgtgctgcac caggactggc tgaacggcaa ggaatacaag   1020
tgcaaggtgt ccaacaaggc cctgcccgct cctatcgaaa agaccatctc caaggccaag   1080
ggccagcctc gcgagcctca ggtgtacacc ctgcctccct ccgggagga gatgaccaag   1140 aaccaggtgt ccctgacctg cctggtgaag ggcttctacc cttccgacat cgccgtggag   1200
tgggagtcca acggccagcc tgagaacaac tacaagacca cccctcctgt gctggactcc   1260
gacggctcct tcttcctgta ctccaagctg accgtggaca agtccggtg gcagcagggc   1320 aacgtgttct cctgctccgt gatgcacgag gccctgcaca accactacac ccagaagtcc   1380
ctgtccctga gccccggcaa g                                             1401

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: Synthetic
      GS SalI-F primer

<400> SEQUENCE: 3
gtcgacatgg ccacctcagc aagttccc                                        28

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: Synthetic
      GS XbaI-R primer

<400> SEQUENCE: 4
tctagattag tttttgtatt ggaaaggg                                        28

<210> SEQ ID NO 5
<211> LENGTH: 1122
<212> TYPE: DNA
<213> ORGANISM: Unknown
<220> FEATURE:
<223> OTHER INFORMATION: Description of Unknown: Hamster GS
      polynucleotide

<400> SEQUENCE: 5
atggccacct cagcaagttc ccacttgaac aaaaacatca agcaaatgta cttgtgcctg     60
ccccagggtg agaaagtcca agccatgtat atctgggttg atggtactgg agaaggactg    120
cgctgcaaaa cccgcaccct ggactgtgag cccaagtgtg tagaagagtt acctgagtgg    180
aattttgatg gctctagtac ctttcagtct gagggctcca cagtgacat gtatctcagc    240
```

```
cctgttgcca tgtttcggga cccctcccgc agagatccca acaagctggt gttctgtgaa    300
gttttcaagt acaaccggaa gcctgcagag accaatttaa ggcactcgtg taaacggata    360
atggacatgg tgagcaacca gcaccctgg tttggaatgg aacaggagta tactctgatg    420
ggaacagatg gcaccctttt tggttggcct tccaatggct ttcctgggcc ccaaggtccg    480
tattactgtg gtgtgggcgc agacaaagcc tatggcaggg atatcgtgga ggctcactac    540
cgcgcctgct tgtatgctgg ggtcaagatt acaggaacaa atgctgaggt catgcctgcc    600
cagtgggaat tccaaatagg accctgtgaa ggaatccgca tgggagatca tctctgggtg    660
gcccgtttca tcttgcatcg agtatgtgaa gactttgggg taatagcaac ctttgacccc    720
aagcccattc ctgggaactg aatggtgca ggctgccata ccaactttag caccaaggcc    780
atgcgggagg agaatggtct gaagcacatc gaggaggcca tcgagaaact aagcaagcgg    840
caccggtacc acattcgagc ctacgatccc aaggggggcc tggacaatgc ccgtcgtctg    900
actgggttcc acgaaacgtc caacatcaac gacttttctg ctggtgtcgc caatcgcagt    960
gccagcatcc gcattccccg gactgtcggc caggagaaga aaggttactt tgaagaccgc    1020
cgcccctctg ccaattgtga ccccttgca gtgacagaag ccatcgtccg cacatgcctt    1080
ctcaatgaga ctggcgacga gcccttccaa tacaaaaact aa                      1122

<210> SEQ ID NO 6
<211> LENGTH: 373
<212> TYPE: PRT
<213> ORGANISM: Unknown
<220> FEATURE:
<223> OTHER INFORMATION: Description of Unknown: Hamster GS polypeptide

<400> SEQUENCE: 6

Met Ala Thr Ser Ala Ser Ser His Leu Asn Lys Asn Ile Lys Gln Met
1               5                   10                  15

Tyr Leu Cys Leu Pro Gln Gly Glu Lys Val Gln Ala Met Tyr Ile Trp
                20                  25                  30

Val Asp Gly Thr Gly Glu Gly Leu Arg Cys Lys Thr Arg Thr Leu Asp
            35                  40                  45

Cys Glu Pro Lys Cys Val Glu Glu Leu Pro Glu Trp Asn Phe Asp Gly
        50                  55                  60

Ser Ser Thr Phe Gln Ser Glu Gly Ser Asn Ser Asp Met Tyr Leu Ser
65                  70                  75                  80

Pro Val Ala Met Phe Arg Asp Pro Phe Arg Arg Asp Pro Asn Lys Leu
                85                  90                  95

Val Phe Cys Glu Val Phe Lys Tyr Asn Arg Lys Pro Ala Glu Thr Asn
            100                 105                 110

Leu Arg His Ser Cys Lys Arg Ile Met Asp Met Val Ser Asn Gln His
        115                 120                 125

Pro Trp Phe Gly Met Glu Gln Glu Tyr Thr Leu Met Gly Thr Asp Gly
    130                 135                 140

His Pro Phe Gly Trp Pro Ser Asn Gly Phe Pro Gly Pro Gln Gly Pro
145                 150                 155                 160

Tyr Tyr Cys Gly Val Gly Ala Asp Lys Ala Tyr Gly Arg Asp Ile Val
                165                 170                 175

Glu Ala His Tyr Arg Ala Cys Leu Tyr Ala Gly Val Lys Ile Thr Gly
            180                 185                 190

Thr Asn Ala Glu Val Met Pro Ala Gln Trp Glu Phe Gln Ile Gly Pro
        195                 200                 205
```

```
Cys Glu Gly Ile Arg Met Gly Asp His Leu Trp Val Ala Arg Phe Ile
    210             215                 220

Leu His Arg Val Cys Glu Asp Phe Gly Val Ile Ala Thr Phe Asp Pro
225             230                 235

Lys Pro Ile Pro Gly Asn Trp Asn Gly Ala Gly Cys His Thr Asn Phe
                245                 250                 255

Ser Thr Lys Ala Met Arg Glu Glu Asn Gly Leu Lys His Ile Glu Glu
            260             265             270

Ala Ile Glu Lys Leu Ser Lys Arg His Arg Tyr His Ile Arg Ala Tyr
            275             280             285

Asp Pro Lys Gly Gly Leu Asp Asn Ala Arg Arg Leu Thr Gly Phe His
    290             295             300

Glu Thr Ser Asn Ile Asn Asp Phe Ser Ala Gly Val Ala Asn Arg Ser
305             310             315                 320

Ala Ser Ile Arg Ile Pro Arg Thr Val Gly Gln Glu Lys Lys Gly Tyr
            325             330             335

Phe Glu Asp Arg Arg Pro Ser Ala Asn Cys Asp Pro Phe Ala Val Thr
            340             345             350

Glu Ala Ile Val Arg Thr Cys Leu Leu Asn Glu Thr Gly Asp Glu Pro
        355             360             365

Phe Gln Tyr Lys Asn
370
```